United States Patent [19]
Bunce et al.

[11] Patent Number: 5,881,721
[45] Date of Patent: Mar. 16, 1999

[54] APPARATUS FOR ORIENTING AND POSITIONING AN ELONGATE OBJECT FOR DISPENSING

[75] Inventors: Martin Bunce; John Lamb; Martin Greeves, all of Wiltshire; Iain Grierson McDerment, Herts, all of Great Britain; Peter Villax, Lisbon, Portugal

[73] Assignee: Plurichemie Anstalt, Liechtenstein

[21] Appl. No.: 880,496

[22] Filed: Jun. 23, 1997

[30] Foreign Application Priority Data

Apr. 4, 1997 [PT] Portugal .................................. 101.988

[51] Int. Cl.⁶ .................................................. A61M 15/00
[52] U.S. Cl. ............................... 128/203.21; 128/203.15; 221/265
[58] Field of Search ......................... 128/203.21, 203.15, 128/203.23, 203.13; 604/50, 58; 221/265

[56] References Cited

U.S. PATENT DOCUMENTS

| | | | |
|---|---|---|---|
| 2,630,245 | 3/1953 | Maier | 221/265 |
| 4,860,740 | 8/1989 | Kirk et al. | 128/203.15 |
| 5,048,514 | 9/1991 | Ramella | 128/203.21 |
| 5,207,217 | 5/1993 | Cocozza et al. | 128/203.21 |
| 5,372,128 | 12/1994 | Haber et al. | 128/203.21 |
| 5,379,763 | 1/1995 | Martin | 128/203.15 |

FOREIGN PATENT DOCUMENTS

| | | |
|---|---|---|
| 528764 A1 | 2/1993 | European Pat. Off. . |
| 528764 B1 | 2/1993 | European Pat. Off. . |
| 92 03175 | 3/1992 | WIPO . |
| 94 14491 | 7/1994 | WIPO . |

*Primary Examiner*—John G. Weiss
*Assistant Examiner*—Charles W. Anderson
*Attorney, Agent, or Firm*—Ostrolenk, Faber, Gerb & Soffen, LLP

[57] ABSTRACT

Apparatus for orienting elongate objects, for example capsules of medicament, comprises a passage for receiving an individual capsule in a preferred orientation, a container for holding a bulk supply of capsules, and a ramp surface which directs a capsule towards the passage when the device is positioned such that the passage extends vertically downwardly from the container. It has been found that by appropriate choice of ramp angle, passage diameter and container diameter there is a high probability that a single capsule will be loaded into the dispensing passage when the apparatus is inverted to place the dispensing passage below the bulk supply. The apparatus is particularly useful in a dry medicament dispensing apparatus comprising, in addition to the orienting apparatus, a chamber for receiving capsules from the dispensing passage, means for piercing the ends of the capsule, and a mouthpiece for drawing air through the capsule and to entrain the medicament.

17 Claims, 1 Drawing Sheet

APPARATUS FOR ORIENTING AND POSITIONING AN ELONGATE OBJECT FOR DISPENSING

The present invention relates to apparatus for dispensing elongate objects one by one in a way that prevents them from jamming.

The invention is particularly suitable for the controlled dispensing of capsules containing pharmaceutical or therapeutic agents. However, it is to be understood that the invention is not limited to this application and that, on the contrary, the invention has a wide range of applications in the dispensing of many types of elongate object.

Until now, systems which dispense capsules for pharmaceutical use in devices holding several capsules have stored them separately in bulk containers in a random orientation. Typical bulk containers are known capsule jars or bottles where the only way to use them has been to take them one at a time, by hand, for use. Due to the small size of a capsule, a certain amount of dexterity is necessary, making this difficult for use by elderly users.

For the purpose of counting them, say by a pharmacist dispensing a certain number of capsules from a large container, the usual way has been to pour them into an appropriate tray where separation and counting could be facilitated. In the case of inhalation devices employing capsules containing a unit dose of powder, the only way to store several capsules inside the inhaler device has been to insert them in an ordered way and then to ensure that the capsules were kept in such an ordered state. This is because capsules used for inhalation need to be pierced at precise points, requiring that the capsule be presented to the piercing or cutting mechanism always in the same position.

Patent U.S. Pat. No. 5,048,514 describes an inhalation device where capsules are stored end-to-end and are dispensed into a chamber by gravity. U.S. patent application 08/382,428, now U.S. Pat. No. 5,673,428 equivalent to EP-A-0666085, describes a similar arrangement but stores the capsules in narrow tubes to dispense them vertically, one-by-one, into a capsule chamber. The diameter of the chamber is only barely wider than the capsule itself requiring that the capsule be presented vertically and aligned with the chamber, otherwise the capsule will jam and fail to be inserted properly. In both devices, capsules have to be loaded by hand into narrow channels.

The inhaler device described in U.S. Pat. No. 5,372,128 exhibits a capsule cassette shaped like a revolver magazine and holding one capsule in each of the six compartments, side-by-side. The specification further describes the possibility of the inhaler holding many such cassettes. In use, this inhaler would have to be laboriously filled by hand or have the cassettes pre-filled with a machine capable of inserting one capsule per compartment. Simple pouring would not be a viable filling method.

Many other patent publications, for example EPA-0 528 764; U.S. Pat. No. 4,860,740; WO 94/14491 and WO 92/03175, describe inhalers provided with a magazine or tray where the capsules must first be inserted in appropriate compartments or positions.

All such inhalers require that the capsules be carefully inserted in the desired orientation in narrow channels, in the case of end-to-end orientation, or on mounting trays, in the case of side-by-side orientation. This has required careful manual insertion and a level of dexterity which elderly patients or young children cannot achieve; alternatively expensive machinery is used in large scale production to insert the capsules into the channels, magazines or trays in the desired orientation, which adds to the cost.

Until now, there has been no system whereby capsules could be inserted at random, for instance through pouring, into a capsule inhaler where a simple mechanism, preferably relying on gravity, could re-orient capsules from a random orientation into an ordered orientation and thereby permit dispensing. The elongate shape of pharmaceutical capsules, such as those manufactured from gelatine or the more recent hydroxypropyl methyl cellulose capsules prevented an error-free re-orientation and thus such gravity-based orientation systems were never incorporated into inhalers employing capsules.

We have found a new way to orient capsules within a container, whereby they can be reliably dispensed one-by-one from the container under the influence of gravity. Throughout the present application, the word "capsule" means any item having the general shape of a conventional pharmaceutical capsule and shall not have a meaning defined by the type, nature, use and ingredients of different types of capsules, unless a specific example be given or unless specifically stated otherwise.

According to one aspect of the present invention, there is provided apparatus for orienting and positioning an elongate object for dispensing from the apparatus in an end-on orientation, the apparatus comprising: a tube for receiving the object to be oriented and dispensed; an elongate dispensing passage having a diameter less than that of the tube extending from an inlet end of the passage located adjacent the wall of the tube to a dispensing outlet, the passage being sized to receive the object to be dispensed only when the axis of the object is generally parallel to the axis of the passage; and a ramp surface extending from the inlet end of the passage obliquely across the tube to the opposite wall thereof in the direction towards the end of the tube opposite the inlet passage whereby when the apparatus is positioned with the axis of the passage substantially vertical an elongate object located in the tube will be guided by the ramp surface towards the inlet end of the passage.

The ramp is angled so that the plane of the ramp rises towards the dispensing end of the tube, finally occupying almost the entire cross-section of the tube extremity. The ramp is therefore at an angle with the longitudinal axis of the tube. The face of the ramp is smooth and is preferably flat. The passage is sufficiently wide to allow just one capsule therethrough, so that the longitudinal axis of the capsule is also parallel to the axis of the passage. This passage communicates with the outside of the cylindrical tube.

In use, the space available inside the tube can be filled with capsules, but preferably some space is left free, so that the capsules may freely move about inside the tube and re-orient from one random order to another. When the tube is placed vertically with its dispensing end pointing down, the capsules will be free to tumble down the tube against the ramp, as a consequence of which the first one down will become vertically oriented and enter the passage via its inlet end which is situated in the ramp, slide therethrough down to the dispensing end of the tube and exit, as a result of gravity.

In some cases, the capsule may not be properly oriented and dispensed by just placing the tube vertically. In this case, a slight agitation of the tube by hand will be sufficient for proper orientation, insertion and exit of the capsule.

Successful operation results from the force of gravity acting upon the capsules inside the cylindrical tube where they become increasingly constrained by the ramp, so that one capsule is forced out through the passage. The angle of the ramp is important, but good operation will occur across a very broad range of angles.

Ramp angles may range from very steep to very shallow. Other things being equal, the angle determines the rate of success in capsule orientation. With an angle approaching 90°, that is an angle so steep that there is no useful inclination and therefore no guiding influence on the capsule, capsules will still become oriented, but many attempts are required. In experiments where capsules have been placed inside the cylindrical tube where no ramp was provided, a success rate of 16% was recorded through the exit passage. In these successful insertions, the tumbling capsule had by chance become aligned with the dispensing passage just prior to touching it and so was able to slide down it.

At the other extreme, a ramp with a very shallow inclination, say 5°, will be successful in orienting the capsule because its very long inclined plane will assist the capsule in its travel towards the dispensing passage. However, very shallow angles result in excessively long ramps, which are wasteful of space inside the cylindrical tube.

Consequently, while there are angle ranges where the device will be more successful at properly orienting and dispensing the capsule, there is not one angle which will completely prevent it.

This invention can be applied to several applications. For instance, it can be applied to containers holding sweets shaped like a capsule and provided with an easy dispensing system; or it can be applied to any application where there is a need to dispense capsules or capsule-shaped pharmaceutical unit doses. One such application is as a capsule counter and dispenser: a capsule container might be equipped with a dispensing tube which will be short, if the intention is to deliver one capsule at a time or will be long, if the objective is to dispense several capsules at a time, as is the case when there is a need to count capsules.

In a hand-held capsule-counting device, the system needs to be formed by a hopper containing the capsules in random order, the capsule orienting mechanism and a transparent tube ideally provided with capsule locking mechanisms at the beginning and the end of the tube. This length of tube will ideally be some exact multiple of the length of one capsule, so that an exact number of capsules may be contained in a full tube. The hopper, orientation mechanism and tube are disposed in serial connection, so that when positioned vertically, the capsules fall under the force of gravity one by one from the hopper into the orientation mechanism and then into the tube. In order to facilitate the continued movement of capsules through the orientation mechanism, a slight agitation of the entire system may be required and may be provided by hand agitation.

Due to the possible need to agitate the capsule container, there must be some free space, so that the capsules may freely move when the container is shaken.

Another application of this invention is in multi-capsule dry-powder inhalers, resulting in devices which can be filled by hand without the need for inserting the capsules in an ordered way. These devices can now be loaded by simple pouring of capsules from a bulk container into the storage unit of the inhaler. This will be especially useful for less dexterous people, such as the elderly, or for the blind.

The system will now be described in ways that can improve the operation of the capsule dry-powder inhaler of U.S. application Ser. No. 08/382,428, the disclosure whereof is incorporated herein by reference. In that specification and associated drawings, the capsule container was composed of narrow tubes where the capsules were inserted end to end, requiring considerable dexterity.

Fitted with an embodiment of the present invention, the capsule container of the inhaler can be of any shape and size and can contain several capsules stored in a random order. However, in keeping with the overall appearance of the inhaler, the preferred shape for the container is cylindrical. The container is attached by a friction fit or by a screw-thread onto a cylindrical tube where the ramp is located and where the orientation of the capsule will take place.

At the point of attachment of the capsule container, the cylindrical tube should have a free headspace of at least one capsule length and preferably two capsule lengths. This headspace is highly desirable to facilitate the movement of the capsules. The cylindrical tube needs to be wide enough to allow capsules to freely re-orient, but not so wide that too many capsules will jam against each other. While tubes with an internal diameter of less than one capsule length will still feed the capsules, a diameter greater than one capsule length will permit 360° movement of each capsule and ensure the freest motion.

After the free headspace, the cylindrical tube is internally shaped so as to enclose a ramp. The cylindrical tube space is gradually narrowed by the presence of this ramp which widens as it nears the base of the cylindrical tube.

The ramp should have a vertical height of about two capsule heights and a width at its base occupying almost the entire cross-section of the cylindrical tube. The face of the ramp is smooth and flat. Half-way down the ramp is defined a round passage, the longitudinal axis of which is parallel that of the cylindrical tube. The edges of the passage are chamfered or flared to assist in the righting of the capsule. The diameter of this passage is just wide enough for the capsule to slide freely down it in a vertical orientation. If it fails to orient under gravity alone, a slight tilt or shaking of the inhaler will be sufficient for the capsule to re-orient vertically into the passage.

The diameter of the passage determines the preferred diameter of the cylindrical tube, which should be around three passage diameters or less: this leaves, between the edge of the passage and the wall of the tube, only space for a standing capsule, an inherently unstable position from which the capsule will fall into the passage.

Once the capsule has entered the round passage in the ramp it is properly oriented and can slide down to the capsule chamber in the barrel of the inhaler described in U.S. application Ser. No. 08/382,428 where it is then pierced, inhaled and ejected as described therein.

The capsule container, cylindrical tube and the ramp can be made of plastic or any other suitable material which can be suitably moulded or manufactured; the cylindrical tube will be preferably moulded from clear plastic, so that the remaining number of capsules inside the inhaler and their successful orientation can be visually checked by the user.

An important feature of the present invention is in the internal configuration of the tube, which allows the force of gravity to orient a capsule between the flat surface of the ramp and the round surface of the cylindrical tube, down a passage. A ramp with an angle of 30° achieves a high rate of success in feeding and orienting several randomly stored capsules. Experiments with 40 capsules stored in the capsule container with a free headspace of at least two capsule lengths have demonstrated an orientation success rate in excess of 80% with gravity alone (just turning the inhaler upside down) and 100% with a little agitation.

The dimensions of the orienting system, such as ramp angle and height, cylindrical tube height and width and passage width are important and the combination of certain dimensions which have been disclosed will result in good operation. For different sizes of capsule, other dimensions will result in equally high success rates, but it should be noted that it is the ramp enclosed inside a cylindrical tube and comprising a passage which is desirable for successful and regular orientation. Other shapes were tried, for instance an inverted cone feeding the passage (a funnel) but this was highly prone to jamming and while some cone shapes worked better than others, the success rate in capsule orientation and dispensing was generally low.

The capsule container is not essential to the invention: the orientation system can be used in an embodiment of the inhaler intended to be used just once or to receive just one capsule at a time in which case there is no need for a container. This is the case of single-dose vaccines, anaesthetics or expensive drugs such as peptides or proteins where it is not necessary or advisable to carry several unit doses of drug inside the inhaler. In this case, the patient will just drop one capsule inside the tube of the inhaler, and it will be automatically oriented and inserted into the inhaler barrel. Experiments have shown than when a single capsule is dropped in this manner into an empty inhaler, it always orients successfully, without need for shaking.

For other drugs which need to be taken frequently, such as bronchodilators, corticosteroids and anti-inflammatory drugs used in respiratory diseases or such as insulin for the treatment of diabetics, a capsule container will be useful. A container storing enough capsules for a day of treatment or even weeks of treatment is still sufficiently small for the inhaler to be convenient to be carried inside a pocket.

Examples of drugs which can be held in the capsules used in the present invention include salbutamol, pirbuterol, fenoterol, formoterol, reproterol, rimiterol, tulobuterol, bambuterol, salmeterol, isoprenaline, orciprenaline, adrenaline, ephedrine, terbutaline, sodium cromoglycate, nedocromil, beclomethasone, budesonide, fluticasone, flunisolide, sumatriptan, morphine, insuline, dornase alpha, peptides, proteins, anti-infectives, amino acids and generally pharmaceutically active products which can be beneficially delivered to the lungs or to the nose, for systemic or local effect.

Reference is now made to the accompanying drawings, in which.

Figure 1:
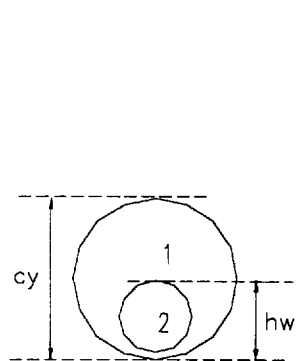
FIGS. 1, 2 and 3 are top, front and side views of part of a device according to the invention.
Figure 2:
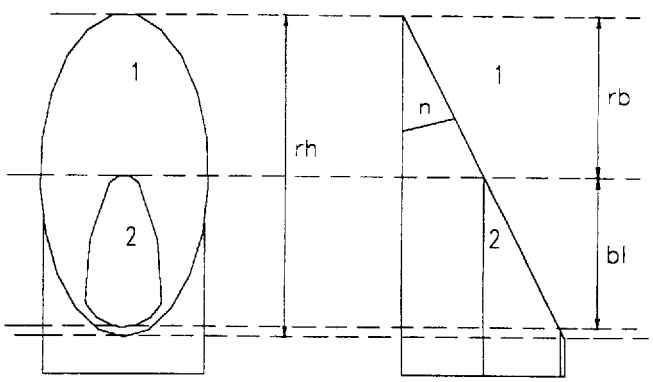
Figure 3:
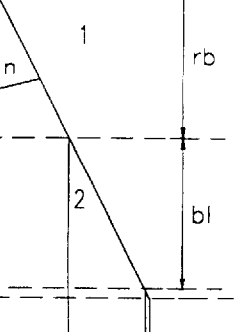

FIGS. 1, 2 and 3 illustrate different perspectives of the ramp, having a straight and flat face 1 and a capsule passage 2. The dimensions of one embodiment of the present invention have been measured and correspond to the letter references inscribed in FIGS. 1, 2 and 3 and disclosed in the present table:

| | | |
|---|---|---|
| Diameter of the cylindrical tube | cy | 16 mm |
| Capsule hole diameter | hw | 7 mm |
| Ramp height | rh | 26 mm |
| Ramp angle | n | 30° |
| Distance from the beginning of the ramp to the beginning of the hole | rb | 16 mm |
| Distance from the beginning of the hole to the lower edge of the hole | bl | 11 mm |

These dimensions are adequate for the correct movement of a pharmaceutical capsule measuring 14.2 mm in length and 5.3 mm in width. However, it should be stressed that proper adaptation of these dimensions to objects with different sizes is readily possible without undue experimentation. Therefore, this invention is not restricted to one capsule size only and not even to capsules: pharmaceutical unit doses or sweets having the general shape of a capsule will equally be usable in the present invention and benefit from it.

Figure 4:
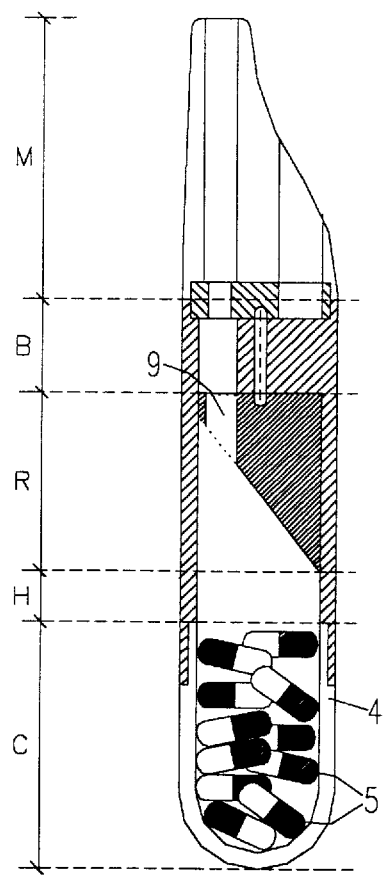
FIG. 4 is a cross-sectional view showing the side of an inhaler described in U.S. application Ser. No. 08/382,428, incorporating a device according to the invention.

FIG. 4 shows the inhaler comprised of a mouthpiece M, a barrel area B, a ramp area R, free headspace H and a capsule container C. The capsule container 4 is filled to the brim with capsules 5.

Figure 5:
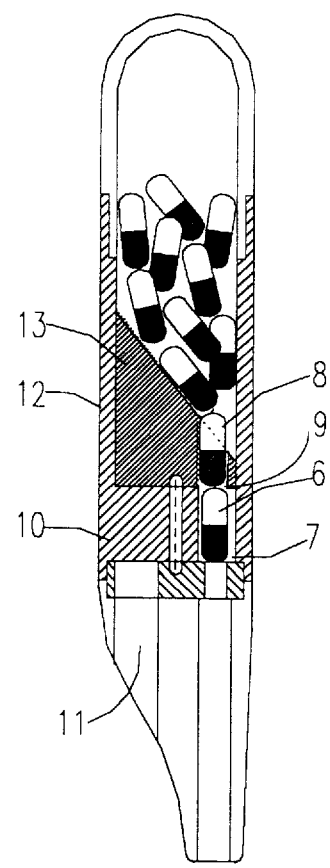
FIG. 5 is a side view of the inhaler of FIG. 4, shown upside down.

FIG. 5 shows the same inhaler which has been turned upside down. The capsules now fill the free headspace and the ramp area and become vertically oriented as they near the passage 9. One capsule 8 is already inserted into the passage 9 and its movement is blocked by the capsule 6 which has preceded it and been dispensed into the capsule chamber 7. The capsule chamber 7 is contained inside a rotating barrel 10.

The operation of the inhaler requires that the once a capsule has been loaded into the capsule chamber 7, the rotating barrel 10 is turned. This movement transports the capsule 6 past two small blades (not shown) which will slit both ends, will then take it to the inhalation position, and finally, after inhalation has taken place, to the ejection position 11. Continuing to turn the rotating barrel 10 will bring the capsule chamber 7 in alignment again with the passage 9 where the next capsule 8 is in place for dispensing.

The rotating barrel 10 is connected to the cylindrical tube 12 and is unconnected to the ramp 13. In operation, the turning motion of the rotating barrel 10 and cylindrical tube 12 is in opposite direction to that of the ramp 13. These opposite turning motions will further assist the righting of the capsules between the ramp 13 and the cylindrical tube 12 and dispensing of the capsule into the passage 9.

What is claimed is:

1. Apparatus for orienting and positioning an elongate object for dispensing from the apparatus in an end-on orientation, the apparatus comprising:

a tube for receiving the object to be oriented and dispensed;

a ramp surface extending substantially across the tube from one wall to an opposite wall thereof; and an elongate dispensing passage having a diameter less than that of the tube and being sized to receive the object to be dispensed only when the axis of the object is generally parallel to the axis of the passage, the passage extending from an inlet end formed by an aperture in the ramp surface to a dispensing outlet, the passage being adjacent the one wall of the tube such that the axis of the passage is parallel to but radially offset from an axis of the tube, whereby when the apparatus is positioned with the passage below the tube and the axis of the passage substantially vertical, an elongate object located in the tube will be guided by the ramp surface towards the inlet end of the passage.

2. Apparatus according to claim 1 wherein the ramp surface is substantially flat.

3. Apparatus according to claim 1 wherein the inlet end of the passage is outwardly flared.

4. Apparatus according to claim 1 wherein the passage is of a length to receive a plurality of objects end-to-end.

5. Apparatus according to claim 1 wherein the tube extends beyond the end of the ramp surface remote from the passage, in the direction away from the inlet end of the passage, by a distance of greater than the length of the object and preferably equal to twice the length of the object.

6. Apparatus according to claim 1 wherein the diameter of the tube is three times or less than the diameter of the passage.

7. Apparatus according to claim 1 wherein the surface of the ramp extends at an angle of between 5° and 70° to the longitudinal axis of the tube.

8. Apparatus according to claim 1 wherein the ramp surface is substantially flat.

9. Apparatus according to claim 1 wherein the surface of the ramp extends at an angle of between 25° and 35° to the longitudinal axis of the tube.

10. A dry powder inhaler comprising a dispensing chamber and apparatus for loading an elongate capsule of dry powder material into said dispensing chamber of the inhaler, the apparatus comprising:

a tube for receiving the object to be oriented and dispensed;

a ramp surface extending substantially across the tube from one wall to an opposite wall thereof; and an elongate dispensing passage having a diameter less than that of the tube and being sized to receive the object to be dispensed only when the axis of the object is generally parallel to the axis of the passage, the passage extending from an inlet end formed by an aperture in the ramps surface to a dispensing outlet, the passage being adjacent the one wall of the tube such that the axis of the passage is parallel to but radially offset from an axis of the tube, whereby when the apparatus is positioned with the passage below the tube and the axis of the passage substantially vertical, an elongate object located in the tube will be guided by the ramp surface towards the inlet end of the passage.

11. The combination of an elongate object and an apparatus for orienting and positioning the elongate object for dispensing from the apparatus in an end-on orientation, the apparatus comprising:

a tube for receiving the object to be oriented and dispensed;

a ramp surface extending substantially across the tube from one wall to an opposite wall thereof; and an elongate dispensing passage having a diameter less than that of the tube and being sized to receive the object to be dispensed only when the axis of the object is generally parallel to the axis of the passage, the passage extending from an inlet end formed by an aperture in the ramp surface to a dispensing outlet, the passage being adjacent the one wall of the tube such that the axis of the passage is parallel to but radially offset from an axis of the tube, whereby when the apparatus is positioned with the passage below the tube and the axis of the passage substantially vertical, an elongate object located in the tube will be guided by the ramp surface towards the inlet end of the passage.

12. Apparatus according to claim 11 wherein the diameter of the tube is greater than the length of the object.

13. Apparatus according to claim 11 wherein the extent of the ramp, measured along the axis of the tube, is greater than the length of the object.

14. Apparatus according to claim 11 including means for closing the tube at the end thereof remote from the ramp surface to form a container for receiving and storing a plurality of objects to be dispensed.

15. Apparatus according to claim 14 having a multiplicity of objects to be dispensed located within the container, said objects to be dispensed being elongate capsules containing a medicinal or therapeutic agent.

16. Apparatus according to claim 15 wherein the capsules contain a pharmaceutical composition in powder form and wherein the apparatus is provided with means for receiving a capsule from the passage and means for piercing the capsule to permit dispensing of the contents thereof.

17. Apparatus according to claim 16 wherein the apparatus comprises means for dispensing the contents of the capsule by passage of inhaled air through the capsule.

* * * * *